(12) United States Patent
Song (10) Patent No.: US 9,895,094 B2
(45) Date of Patent: Feb. 20, 2018

(54) LATERAL FLOW DEVICE FOR ATTACHMENT TO AN ABSORBENT ARTICLE

(71) Applicant: Kimberly-Clark Worldwide, Inc., Neenah, WI (US)

(72) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 122 days.

(21) Appl. No.: 14/450,901

(22) Filed: Aug. 4, 2014

(65) Prior Publication Data
US 2015/0025347 A1    Jan. 22, 2015

Related U.S. Application Data

(63) Continuation of application No. 11/741,943, filed on Apr. 30, 2007, now abandoned.

(51) Int. Cl.
*A61B 5/20*  (2006.01)
*A61B 10/00* (2006.01)
(Continued)

(52) U.S. Cl.
CPC ............ *A61B 5/207* (2013.01); *A61B 10/007* (2013.01); *A61F 13/42* (2013.01);
(Continued)

(58) Field of Classification Search
CPC .... A61F 13/42; A61F 13/84; A61F 2013/427; A61F 2013/429; A61F 2013/8473; A61F 2013/8488; A61F 2013/8491
See application file for complete search history.

(56) References Cited

U.S. PATENT DOCUMENTS 3,918,433 A   11/1975 Fuisz
4,637,979 A   1/1987 Skjold et al.
(Continued)

FOREIGN PATENT DOCUMENTS

DE    3810473    10/1989
DE   29709497    9/1997
(Continued)

OTHER PUBLICATIONS

Patent Abstract of JP3210193 of Kawanishi, Sep. 1991, 1 page.
Search Report and Written Opinion for PCT/IB2008/050802 dated Nov. 11. 2008, 12 pages.

*Primary Examiner* — Lynne Anderson
(74) *Attorney, Agent, or Firm* — Dority & Manning, P.A.

(57) ABSTRACT

A lateral flow device for testing a bodily fluid, such as urine, blood, mucous, saliva, etc., is provided. The lateral flow device is configured to be attached to an absorbent article via an attachment mechanism located on the lateral flow device or the absorbent article. The lateral flow device includes a chromatographic medium (e.g., porous membrane) that defines a detection zone that provides a signal indicative of the presence or absence of the analyte. The device may also include a control zone that provides a signal indicative of whether a sufficient amount of bodily fluid has been provided and tested. Regardless of its specific configuration, the lateral flow device is configured to be attached onto the absorbent article to provide a user or caregiver with rapid information about a health condition. For example, the device may be attached onto a diaper to provide information about the presence of enzymes or other compounds often encountered with a patient having a urinary tract infection. This information may provide an early warning system to allow the user or caregiver to seek additional testing and/or (Continued)

treatment. Alternatively, semi-quantitative or quantitative results may be derived from the test.

25 Claims, 7 Drawing Sheets

(51) Int. Cl.
    *A61F 13/42*     (2006.01)
    *G01N 33/558*     (2006.01)
    *G01N 33/543*     (2006.01)
    *A61F 13/84*     (2006.01)

(52) U.S. Cl.
    CPC ..... *G01N 33/54306* (2013.01); *G01N 33/558* (2013.01); *A61B 2010/0006* (2013.01); *A61F 2013/8473* (2013.01); *A61F 2013/8488* (2013.01); *G01N 2800/348* (2013.01)

(56) References Cited

U.S. PATENT DOCUMENTS

| | | |
|---|---|---|
| 4,657,855 A | 4/1987 | Corey et al. |
| 4,704,116 A | 11/1987 | Enloe |
| 4,806,423 A | 2/1989 | Hugl et al. |
| 4,814,271 A | 3/1989 | Hugl et al. |
| 5,075,077 A | 12/1991 | Durley, III et al. |
| 5,181,905 A | 1/1993 | Flam |
| 5,192,606 A | 3/1993 | Proxmire et al. |
| 5,217,444 A | 6/1993 | Schoenfeld |
| 5,252,459 A | 10/1993 | Tarcha et al. |
| 5,399,219 A | 3/1995 | Roessler et al. |
| 5,464,739 A | 11/1995 | Johnson et al. |
| 5,468,236 A | 11/1995 | Everhart |
| 5,486,166 A | 1/1996 | Bishop et al. |
| 5,490,846 A | 2/1996 | Ellis et al. |
| 5,540,796 A | 7/1996 | Fries |
| 5,595,618 A | 1/1997 | Fries et al. |
| 5,663,044 A | 9/1997 | Noffsinger et al. |
| 5,670,381 A | 9/1997 | Jou et al. |
| 5,702,377 A | 12/1997 | Collier, IV et al. |
| 5,750,359 A | 5/1998 | Huh et al. |
| 5,823,953 A | 10/1998 | Roskin et al. |
| 5,931,823 A | 8/1999 | Stokes et al. |
| 6,060,638 A | 5/2000 | Paul et al. |
| 6,106,461 A | 8/2000 | Roskin |
| 6,126,597 A | 10/2000 | Smith et al. |
| 6,150,002 A | 11/2000 | Varona |
| 6,203,496 B1 | 3/2001 | Gael et al. |
| 6,342,037 B1 | 1/2002 | Roe |
| 6,399,853 B1 | 6/2002 | Roe |
| 6,464,635 B1 | 10/2002 | Cerrato |
| 6,479,727 B1 | 11/2002 | Roe |
| 6,627,394 B2 | 9/2003 | Kritzman |
| 6,663,611 B2 | 12/2003 | Blaney et al. |
| 7,365,238 B2 | 4/2008 | Diehl et al. |
| 7,592,020 B2 * | 9/2009 | Boga ............... A61L 15/56 424/400 |
| 8,012,761 B2 * | 9/2011 | Boga ............... A61F 13/15 435/20 |
| 8,043,272 B2 * | 10/2011 | Long ............... A61F 13/505 600/573 |
| 2003/0124739 A1 | 7/2003 | Song et al. |
| 2004/0100376 A1 * | 5/2004 | Lye ............... A61B 5/411 340/539.12 |
| 2004/0102750 A1 | 5/2004 | Jameson |
| 2004/0133090 A1 | 7/2004 | Dostoinov et al. |
| 2005/0054255 A1 | 3/2005 | Morman et al. |
| 2005/0059941 A1 | 3/2005 | Baldwin et al. |
| 2005/0131287 A1 | 6/2005 | Kaylor et al. |
| 2006/0025732 A1 | 2/2006 | Ying et al. |
| 2006/0069362 A1 | 3/2006 | Odorzynski et al. |
| 2006/0127886 A1 * | 6/2006 | Kaylor ............... G01N 33/558 435/5 |
| 2008/0021423 A1 | 1/2008 | Klofta et al. |
| 2008/0103414 A1 | 5/2008 | Song |

FOREIGN PATENT DOCUMENTS

| | | |
|---|---|---|
| GB | 2022423 A | 12/1979 |
| JP | 3210193 A1 | 9/1991 |
| WO | WO 9424557 A1 | 10/1994 |
| WO | WO 9516425 | 6/1995 |
| WO | WO 0004822 A1 | 2/2000 |
| WO | WO 2007027353 A2 | 3/2007 |

* cited by examiner

LATERAL FLOW DEVICE FOR ATTACHMENT TO AN ABSORBENT ARTICLE

PRIORITY INFORMATION

The present application claims priority to, and is a continuation application of, U.S. patent application Ser. No. 11/741,943 of Xuedong Song titled "Lateral Flow Device for Attachment to an Absorbent Article" filed on Apr. 30, 2007, the disclosure of which is incorporated by reference herein.

BACKGROUND OF THE INVENTION

Multiple tests have been developed for detecting components in urine. Such tests can provide information about overall health as well as provide an indication of a health problem. When timely administered, such tests may also be able to provide an early indication of a health problem, which may be very advantageous for effective treatment. By way of examples, urine testing can be used to detect urinary tract infections, diabetes (including diabetic ketoacidosis), parasites, dehydration, dietary defects, cancer, high blood pressure, kidney disease, asthma, severe emphysema, alcoholism, systemic lupus erythematosus (SLE), glomerulonephritis, and leukemia.

Such tests may be performed by having a patient voluntarily collect and provide a sample. However, patient collected urine samples may not be readily available with certain test subjects such as children, elderly adults, and injured or non-ambulatory patients. Additionally, it may be preferable to collect and test urine samples from these subjects at certain times or conditions where the patient is not necessarily in the presence of medical or otherwise specially trained personnel. Frequently, such subjects may be provided with a diaper or other absorbent article to collect urine. Then, the soiled article is provided to the medical or otherwise specially trained personnel for testing.

As such, a need exists for a device capable of testing bodily fluid that can be attached to an absorbent article such that the testing occurs at the time of the insult of the absorbent article.

SUMMARY OF THE INVENTION

In general, an absorbent article for testing a bodily fluid suspected of containing an analyte is disclosed. The absorbent article comprises an outer cover, a bodyside liner, and an absorbent core positioned between the outer cover and the bodyside liner. A lateral flow device is attached to the bodyside liner of the absorbent article. The lateral flow device includes a chromatographic medium that defines a detection zone. The detection zone is configured for exhibiting a signal indicative of the presence or absence of the analyte in the bodily fluid.

In another embodiment, the present invention is generally directed to an insert for testing a bodily fluid suspected of containing analyte. The insert includes a cover encasing a lateral flow device. Also, the insert includes an attachment mechanism configured to attach the insert to a bodyside liner of an absorbent article. In one embodiment, the insert can also include an absorbent material encased within the cover.

In yet another embodiment, a method for detecting the presence or absence of an analyte in urine is disclosed. The method includes attaching a lateral flow device to a bodyside liner of an absorbent article.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a lateral flow device for testing a bodily fluid (e.g., urine, blood, mucous, saliva, etc.) that can be attached to an absorbent article. Since lateral flow devices are utilized to detect the presence or absence of compounds in a bodily fluid, the manufacturing and packaging environment of the device is controlled to prevent contamination of the device prior to its use. Controlling the manufacturing environment adds costs to the manufacture of the device. If the device were to be integrated within the construction of the absorbent article (e.g., positioned within the absorbent article's construction), then the manufacturing environment of the entire absorbent article would have to be controlled in order to prevent contamination of the device prior to its use, adding significant manufacturing and packaging costs to the absorbent article. However, according to the present invention, the lateral flow device can be separately manufactured under a controlled environment, and then attached to an absorbent article by the user or caregiver. Thus, only the manufacturing environment of the lateral flow device is subject to regulation, saving the cost of regulating the manufacturing environment of the absorbent article.

The lateral flow assay device generally includes a chromatographic medium (e.g., porous membrane) that defines a detection zone for providing a signal indicative of the presence or absence of an analyte. The device may also include a control zone that provides a signal indicative of whether a sufficient amount of bodily fluid has been provided and tested. Regardless of its specific configuration, the lateral flow assay device is configured to be attached to the absorbent article to provide a user or caregiver with rapid information about a health condition. For example, the device may be attached to a diaper to provide information about the presence of enzymes or other compounds often encountered with a patient having a urinary tract infection. This information may provide an early warning system to allow the user or caregiver to seek additional testing and/or treatment. Alternatively, semi-quantitative or quantitative results may be derived from the test.

I. Lateral Flow Assay Device

Generally speaking, a lateral flow assay device is employed in the present invention to perform a heterogeneous assay. A heterogeneous assay is one in which a species is separated from another species prior to detection. Separation may be carried out by physical separation, e.g., by transferring one of the species to another reaction vessel, filtration, centrifugation, chromatography, solid phase capture, magnetic separation, and so forth. The separation may also be nonphysical in that no transfer of one or both of the species is conducted, but the species are separated from one another in situ. In some embodiments, for example, a heterogeneous immunoassay is performed that utilizes mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a fluid test sample. In other embodiments, however, the heterogeneous assay may employ non-specific chemical reactions to achieve the desired separation.

Figure 1:
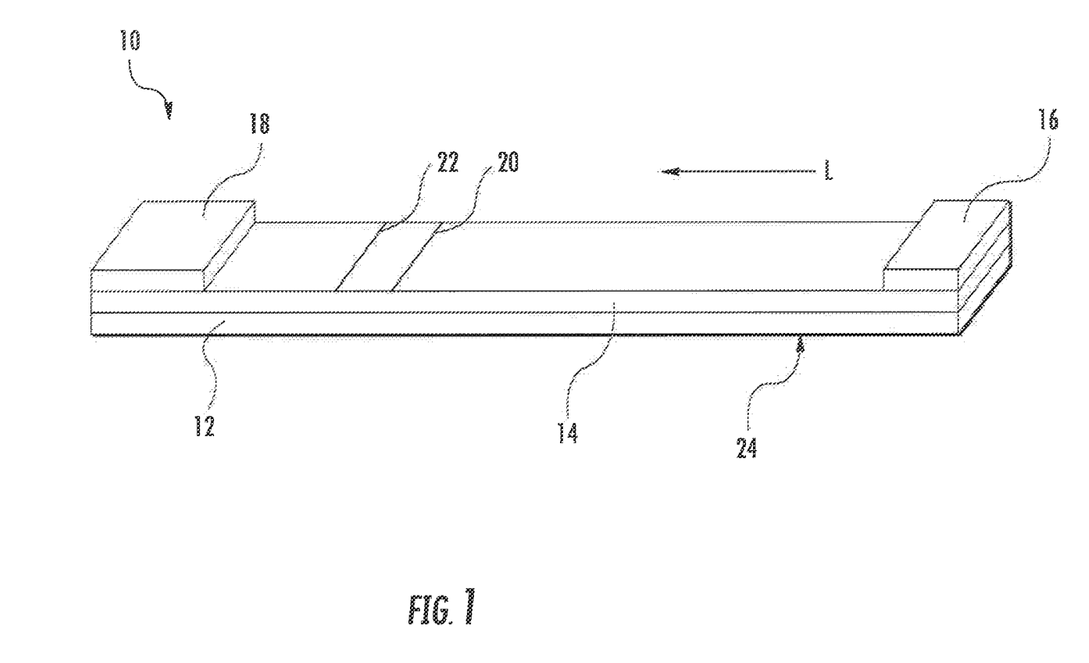
FIG. 1 is a perspective view of an exemplary lateral flow device in accordance with one embodiment of the present invention.

In any event, the use of a lateral flow assay device provides a variety of benefits, including a more uniform flow of the bodily fluid and reagents during testing. This may enhance the accuracy of the test and minimize the need for external control mechanisms. Referring to FIG. 1, for example, one embodiment of a lateral flow assay device 10 will now be described in more detail. As shown, the device 10 contains a chromatographic medium 14 optionally supported by a rigid support 12. The chromatographic medium 14 may be made from any of a variety of materials through which the test sample is capable of passing. For example, the chromatographic medium 14 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 14 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 14 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 12 carries the chromatographic medium 14. For example, the support 12 may be positioned directly adjacent to the chromatographic medium 14 as shown in FIG. 1, or one or more intervening layers may be positioned between the chromatographic medium 14 and the support 12. Regardless, the support 12 may generally be formed from any material able to carry the chromatographic medium 14. The support 12 may be formed from a material that is transmissive to light, such as transparent or optically diffuse (e.g., transluscent) materials. Also, it is generally desired that the support 12 is liquid-impermeable so that fluid flowing through the medium 14 does not leak through the support 12. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 14, the support 12 is generally selected to have a certain minimum thickness. Likewise, the thickness of the support 12 is typically not so large as to adversely affect its optical properties. Thus, for example, the support 12 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

The chromatographic medium 14 may be cast onto the support 12, wherein the resulting laminate may be die-cut to the desired size and shape. Alternatively, the chromatographic medium 14 may simply be laminated to the support 12 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 10 may also contain an absorbent material 18 that is positioned adjacent to the medium 14. The absorbent material 18 can help promote capillary action and fluid flow through the medium 14. In addition, the absorbent material 18 receives fluid that has migrated through the entire chromatographic medium 14 and thus draws any unreacted components away from the detection region to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of an analyte, the bodily fluid (e.g., urine) may be applied to a portion of the chromatographic medium 14 through which it may then travel in the direction illustrated by arrow "L" in FIG. 1. Alternatively, the fluid may first contact a sample application zone 16 that is in fluid communication with the chromatographic medium 14. The sample application zone 16 may be defined by a separate pad or material as shown in FIG. 1, or simply defined by the chromatographic medium 14. In the illustrated embodiment, the fluid may travel from the sample application zone 16 to a conjugate pad (not shown) that is placed in communication with one end of the sample pad. The conjugate pad may contain one or more diffusively immobilized reagents, and be formed from a material through which a fluid is capable of passing (e.g., glass fibers). Some suitable materials that may be used to form the absorbent material 18 and/or sample pad include, but are not limited to, nitrocellulose, cellulose, porous polyethylene pads, and glass fiber filter paper. If desired, the sample pad may also contain one or more assay pretreatment reagents, either diffusively or non-diffusively attached thereto.

Regardless of the particular manner in which it is formed, the lateral flow assay device of the present invention employs one or more zones for providing an indicator of the presence of an analyte. More specifically, such zone(s) typically contain a chemical or biological reagent that interacts with the analyte and/or other reagents to generate a signal (e.g., visual signal). Referring again to FIG. 1, for example, the lateral flow assay device 10 includes a detection zone 20 within which a capture reagent is disposed. Typically, the capture reagent is applied in a manner so that it does not substantially diffuse through the matrix of the chromatographic medium 14 (i.e., non-diffusively immobilized). This enables a user to readily detect the change in color that occurs upon reaction of the capture reagent with other compounds. The capture reagent may, for example, form an ionic and/or covalent bond with functional groups present on the surface of the chromatographic medium 14 so that it remains immobilized thereon. For instance, particles, such as described below, may facilitate the immobilization of the reagent at the detection zone 20. Namely, the reagent may be coated onto particles, which are then immobilized on the chromatographic medium 14 of the device 10. In this manner, the reagent is able to readily contact compounds flowing through the medium 14.

Another zone that may be employed in the lateral flow assay device 10 for improving detection accuracy is a control zone 22. The control zone 22 gives a signal to the user that the test is performing properly. More specifically, reagents may be employed that flow through the chromatographic medium 14 upon contact with a sufficient volume of the bodily fluid being tested. These reagents may then be observed, either visually or with an instrument, within the control zone 22. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes.

If desired, one or more of the reagents employed in the assay device may be disposed on particles (sometimes referred to as "beads" or "microbeads"). Among other things, the particles enhance the ability of the reagent to travel through a chromatographic medium. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. Commercially available examples of suitable particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

The location of the detection zone 20 and control zone 22 may vary based on the nature of the test being performed. In the illustrated embodiment, for example, the control zone 22 is defined by the chromatographic medium 14 and positioned downstream from the detection zone 20. In such embodiments, the control zone 22 may contain a material that is non-diffusively immobilized in the manner described above and forms a chemical and/or physical bond with the control reagents. When the control reagents contain latex particles, for instance, the control zone 22 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 22 may simply be defined by a region of the absorbent material 18 to which the control reagents flow after traversing through the chromatographic medium 14.

Regardless of the particular control technique selected, the application of a sufficient volume of the test sample to the device 10 will cause a signal to form within the control zone 22, whether or not the enzyme or other analyte of interest is present. Among the benefits provided by such a control zone is that the user or other personnel are informed that a sufficient volume of test sample has been added without requiring careful measurement or calculation. This provides the ability to use the lateral flow assay device 10 without the need for externally controlling the reaction time, test sample volume, etc. In the case of the elderly, children, or patients unable to communicate clearly, control zone 22 provides an indication that a sample was discharged, collected, and successfully tested.

The detection zone 20, control zone 22, or any other zone employed in the lateral flow assay device 10 may generally provide any number of distinct detection regions so that a user may better determine the concentration of the enzyme or other analyte within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 10. Likewise, in some embodiments, the regions may be disposed in the form of lines in a direction that is substantially parallel to the flow of the test sample through the device 10.

The specific reagents employed in the lateral flow assay device depend on the analyte of interest and the assay technique employed. In one particular embodiment, for example, it may be desirable to detect the presence of leukocytes in urine as an early diagnosis of urinary tract infection ("UTI"). Although leukocytes are normally present in the urine, it has been determined that the threshold limit for pathological levels is about $1 \times 10^4$ leukocytes per milliliter of uncentrifuged urine. When leukocytes are present in urine, leukocyte esterase is produced and may be used as a biomarker for the presence of leukocytes.

A variety of reagents may be used for detecting the presence of the leukocyte esterase enzyme. One such reagent is a substrate that is chemically acted upon or "cleaved" by the enzyme of interest to release a product. For example, the substrate may be an ester that is catalytically hydrolyzed in the presence of leukocyte esterase to yield an aromatic compound. The aromatic esters may include, for instance, indoxyl esters having the following general formula:

wherein, R may be substituted or unsubstituted, and may be an alkyl group, an alkyoxy group, a hydroxyalkyl group, an alkylene group, a fatty acid group, and so forth. In addition, the aromatic rings may also be substituted or unsubstituted. Specific examples include, for instance, indoxyl acetate, indoxyl butyrate, indoxyl laureate, indoxyl stearate, indoxyl ester of a N-blocked amino acid or peptide and thioindoxyl analogs thereof, and N-Tosyl-L-alanine 3-indoxyl ester. Such indoxyl esters are hydrolyzed by the leukocyte esterase to form a benzopyrrole, such as indoxyl, which has the following structure:

Lactate esters may also be used, such as described in U.S. Pat. No. 5,464,739 to Johnson, et al. and U.S. Pat. No. 5,663,044 to Noffsinger, et al., which are incorporated herein in their entirety by reference thereto for all purposes. Lactate esters are generally hydrolyzed by the leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. No. 5,750,359 to Huh, et al.; U.S. Pat. No. 4,657,855 to Corey, et al.; and Japanese Publication No. 03210193 to Kawanishi, et al., which are incorporated herein in their entirety by reference thereto for all purposes.

Typically, the substrate is diffusively immobilized on the lateral flow assay device 10 prior to application of the urine or other bodily fluid. The substrate is preferably disposed downstream from the sample application zone 16. In this manner, the test sample is capable of mixing with the enzyme upon application. If desired, the pH may be maintained at a relatively neutral level to facilitate the desired enzyme-catalyzed reaction, such as described above. To accomplish the desired pH level, a buffer may be mixed with the substrate prior to application to the device 10. Alternatively, the buffer may be separately applied to the lateral flow assay device 10 so that it is capable of mixing with the reagents upon exposure the bodily fluid being tested.

Regardless, an aromatic compound is released through cleavage of the substrate that is capable of inducing a color change in the presence of certain reagents. The released aromatic compound is a nucleophile in that it contains a group that is electron rich (e.g., amine) and that may form bonds with electron deficient groups. For example, indoxyl esters are hydrolyzed by the leukocyte esterase to form indoxyl. Indoxyl contains an electron-rich, aromatic ring system that is capable of undergoing electrophilic attack by a diazonium ion having the generic formula:

The diazonium ion may be zwitterionic in that the counterion of the diazonium moiety is covalently bound to the ring system. The ring system of the diazonium ion may be substituted or unsubstituted. The ion may be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

Other suitable diazonium salts are classified by the common names "Fast Red B" and "Fast Blue B." Still other suitable diazonium salts may be described in U.S. Pat. No. 4,637,979 to Skiold, et al.; U.S. Pat. No. 4,806,423 to Hugh, et al.; and U.S. Pat. No. 4,814,271 to Hugl, et al., which are incorporated herein in their entirety by reference thereto for all purposes.

As indicated above, the nucleophilic aromatic compounds released by the hydrolysis of the substrate are capable of undergoing electrophilic attack by a reagent (e.g., diazonium ion). This reaction is often referred to as "coupling" and results in the formation of another reagent having a different color. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. The absorption shift provides a color difference that is detectable, either visually or through instrumentation, to indicate the presence of leukocyte esterase or other enzymes within the test sample. For example, prior to contact with an infected test sample, the diazonium ion may be colorless or it may possess a certain color. However, after contacting the test sample and reacting with an aromatic compound released by hydrolysis of the substrate, an aromatic azo compound will form that exhibits a color that is different than the initial color of the diazonium ion. Exemplary aromatic azo compounds that may be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene. In one particular embodiment, for instance, "Fast Red RC" (yellow), a diazonium ion, may react with indoxyl to form an aromatic azo compound that is red and has the following general structure (may be substituted or unsubstituted):

Normally, the above-described diazonium ion is immobilized within the detection zone 20 of the lateral flow assay device 10. The diazonium ion may be applied directly to the medium 14 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution may range from about 0.001 to about 100 milligrams per milliliter of solvent, and in some embodiments, from about 0.1 to about 10 milligrams per milliliter of solvent. In one particular embodiment, the detection zone 20 is defined by the chromatographic medium 14 and formed by coating a solution thereon using well-known techniques and then dried. The diazonium ion concentration may be selectively controlled to provide the desired level of detection sensitivity.

Typically, the diazonium ion is applied in a manner so that it does not substantially diffuse through the matrix of the chromatographic medium 14 (i.e., non-diffusively immobilized), which enables a user to readily detect the change in color that occurs upon reaction of the diazonium ion with a nucleophilic aromatic compound. The diazonium ion may form an ionic and/or covalent bond with functional groups present on the surface of the chromatographic medium 14 so that it remains immobilized thereon. For instance, particles, such as described below, may facilitate the immobilization of the diazonium ion at the detection zone 20. Namely, the diazonium ion may be coated onto particles, which are then immobilized on the chromatographic medium 14 of the device 10. In this manner, the diazonium ion is able to readily contact nucleophilic aromatic compounds flowing through the medium 14.

One benefit of the lateral flow assay device is its ability to readily incorporate one or more additional reagent zones to facilitate the desired reactions. By way of example, a reagent zone (not shown) may be utilized. In the illustrated embodiment, the reagent zone may be located such that test sample travels from the sample application zone 16 to a reagent zone that is in fluid communication with the sample application zone 16. The reagent zone may be formed on the medium 14. Alternatively, the reagent zone may be formed from a separate material or pad. Such a reagent pad may be formed from any material through which the test sample is capable of passing, such as glass fibers.

In addition to the zones specified above, the lateral flow assay device 10 may also include other optional zones. For example, the lateral flow assay device 10 may include an accelerator zone (not shown) in which is contained an accelerator for the enzyme-catalyzed substrate reaction. Typically, the accelerator is diffusively immobilized within the accelerator zone in the manner described above so that it may flow through the medium 14 upon contact with the test sample. The location of the accelerator zone may generally vary, so long as it positioned upstream from the detection zone 20. For example, in some embodiments, the accelerator zone may be positioned at a location (e.g., sample application zone 16) that is upstream from the application of the substrate (e.g., reagent zone). Due to the separation provided between the substrate and accelerator, the likelihood of any premature reaction therebetween is thus reduced. It should be understood, however, that the accelerator may nevertheless be combined with the substrate in some applications.

Another zone that may be employed is a quenching zone (not shown). The quenching zone is configured to remove compounds from the test sample that would otherwise interfere with the accuracy of the detection system. For example, contaminants within the test sample (e.g., phenolics, bilirubin, urobilinogen, etc.) may react with the diazonium ion within the detection zone 20 and form an aromatic azo compound, thereby producing a "false negative" result. Thus, the quenching zone may contain a quenching agent, such as a diazonium ion, that is capable of reacting with the reaction contaminants. The quenching agent may be the same or different than the detection agent used within the detection zone 20. Typically, the quenching agent is non-diffusively immobilized within the quenching zone in the manner described above so that it does not flow through the medium 14 and interfere with testing. The location of the quenching zone may vary, but is typically positioned upstream from the detection zone 20 and the location at which the substrate is applied to avoid interference with enzyme detection. For example, in the illustrated embodiment, the quenching zone may be positioned immediately downstream of the sample application zone 16 and over medium 14. Alternatively, the quenching zone may be positioned upstream from the sample application zone 16.

An exemplary method for detecting the presence of leukocyte esterase within a test sample using the device 10 of FIG. 1 will now be described in more detail. Initially, urine containing leukocyte esterase is discharged to the sample application zone 16 and travels in the direction "L" to a reagent zone. At the reagent zone, the esterase is able to mix with and begin to initiate the catalytic reaction. While flowing through the medium, the enzyme and substrate react to release an aromatic product that subsequently couples with a diazonium ion to form a colored aromatic azo compound in the detection zone 20. After the reaction, the detection zone 20 changes color, which may be indicative of urinary tract infection. Due to the nature of the controlled fluid flow, any unreacted substrate travels to the end of the reaction medium so that it is unable to adversely interfere with observance of the aromatic azo compound in the detection region.

Of course, the present invention is by no means limited to the diagnosis of urinary tract infection. Numerous health conditions may be diagnosed through testing of bodily fluids such as urine. Testing for even a single condition may require that multiple different analytes be targeted. By way of example, the assay device may employ specific binding pairs to test for the presence of certain biological analytes (e.g., antibodies, antigens, etc.). Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

Still other analytes of interest may include proteins, enzymes, nitrites, ketones, various bacteria, red or white blood cells, glucose, bilirubin, urobilinogen, and so forth. By way of example, the presence of nitrites in urine may indicate a urinary tract infection or even other bacterial infections in the body. To test for the presence of nitrites, the assay device may, for example, employ a substrate diffusively immobilized on the chromatographic medium that includes both an aromatic amine and another aromatic compound. The amine is selected so that it will react with the nitrite to form a diazonium salt. The salt, in turn, may react with the aromatic compound to generate an azo dye that provides a visual indication, by a color change, that nitrite has been detected.

II. Absorbent Article

In accordance with the present invention, one or more lateral flow assay devices can be attached to an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

In some embodiments, such as those where the lateral flow device has its own attachment mechanism, the absorbent article does not need any special features or configuration. Thus, the absorbent article can have any configuration desired. Alternatively, the absorbent article can be configured for attaching to a lateral flow device, as explained in greater detail below.

Figure 4:
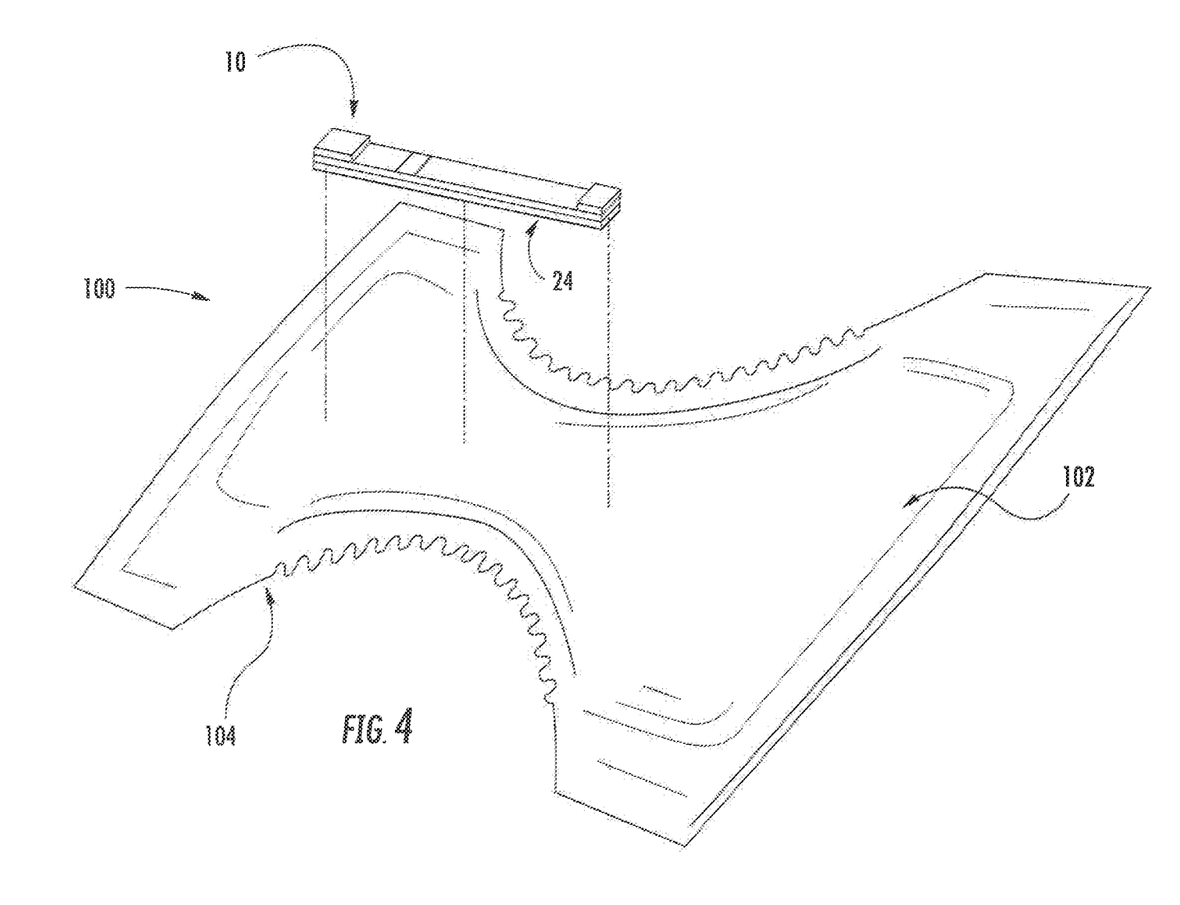
FIG. 4 is a perspective view of an exemplary use of the lateral flow device in conjunction with an absorbent article in accordance with one embodiment of the present invention.

Various embodiments of an absorbent article that may be formed according to the present invention will now be described in more detail. For purposes of illustration only, an absorbent article is shown in FIG. 4 as a diaper 100. In the illustrated embodiment, the diaper 100 is shown as having an hourglass shape in an unfastened configuration. However, other shapes may of course be utilized, such as a generally rectangular shape, T-shape, or I-shape. The diaper 100 includes a chassis formed by various components, generally including an absorbent core positioned between an outer cover 104 and a bodyside liner 102. It should be understood, however, that other layers may also be used in exemplary embodiments of the present invention. For example, a surge layer may be present in the construction of the absorbent article, such as those surge layers described in U.S. Pat. No. 5,486,166 to Ellis, et al. and U.S. Pat. No. 5,490,846 to Ellis, et al., which are incorporated herein in their entirety by reference thereto for all purposes. Likewise, one or more of the layers referred to in FIG. 4 may also be eliminated in certain exemplary embodiments of the present invention.

The bodyside liner 102 is generally employed to help isolate the wearer's skin from liquids held in the absorbent core. For example, the liner 102 presents a bodyfacing surface that is typically compliant, soft feeling, and non-irritating to the wearer's skin. Typically, the liner 102 is also less hydrophilic than the absorbent core so that its surface remains relatively dry to the wearer. As indicated above, the liner 102 may be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The outer cover 104 is typically formed from a material that is substantially impermeable to liquids. For example, the outer cover 104 may be formed from a thin plastic film or other flexible liquid-impermeable material. In one embodiment, the outer cover 104 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 104. If a more cloth-like feeling is desired, the outer cover 104 may be formed from a polyolefin film laminated to a nonwoven web. For example, a stretch-thinned polypropylene film may be thermally laminated to a spunbond web of polypropylene fibers.

Besides the above-mentioned components, the diaper 100 may also contain various other components as is known in the art. For example, the diaper 100 may also contain a substantially hydrophilic tissue wrapsheet (not illustrated) that helps maintain the integrity of the fibrous structure of the absorbent core. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core. The wrapsheet material on one side of the absorbent fibrous mass may be bonded to the wrapsheet located on the opposite side of the fibrous mass to effectively entrap the absorbent core. Furthermore, the diaper may also include a ventilation layer (not shown) that is positioned between the absorbent core and the outer cover 104. When utilized, the ventilation layer may help insulate the outer cover 104 from the absorbent core, thereby reducing dampness in the outer cover 104. Examples of such ventilation layers may include a nonwoven web laminated to a breathable film, such as described in U.S. Pat. No. 6,663,611 to Blaney, et al., which is incorporated herein in its entirety by reference thereto for all purposes.

In some embodiments, the diaper 100 may also include a pair of side panels (or ears) (not shown) that extend from the side edges of the diaper 100 into one of the waist regions. The side panels may be integrally formed with a selected diaper component. For example, the side panels may be integrally formed with the outer cover 104 or from the material employed to provide the top surface. In alternative configurations, the side panels may be provided by members connected and assembled to the outer cover 104, the top surface, between the outer cover 104 and top surface, or in various other configurations. If desired, the side panels may be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 100 may also include a pair of containment flaps that are configured to provide a barrier and to contain the lateral flow of body exudates. The containment flaps may be located along the laterally opposed side edges of the bodyside liner 102 adjacent the side edges of the absorbent core. The containment flaps may extend longitudinally along the entire length of the absorbent core, or may only extend partially along the length of the absorbent core. When the containment flaps are shorter in length than the absorbent core, they may be selectively positioned anywhere along the side edges of diaper 100 in a crotch region 109. In one embodiment, the containment flaps extend along the entire length of the absorbent core to better contain the body exudates. Such containment flaps are generally well known to those skilled in the art. For example, suitable constructions and arrangements for the containment flaps are described in U.S. Pat. No. 4,704,116 to Enloe, which is incorporated herein in its entirety by reference thereto for all purposes.

To provide improved fit and to help reduce leakage of body exudates, the diaper 100 may be elasticized with suitable elastic members, as further explained below. For example, as representatively illustrated in FIG. 4, the diaper 100 may include leg elastics 106 constructed to operably tension the side margins of the diaper 100 to provide elasticized leg bands which can closely fit around the legs of the wearer to reduce leakage and provide improved comfort and appearance. Waist elastics 108 may also be employed to elasticize the end margins of the diaper 100 to provide elasticized waistbands. The waist elastics 108 are configured to provide a resilient, comfortably close fit around the waist of the wearer.

The diaper 100 may also include one or more fasteners. For example, two flexible fasteners can be on opposite side edges of waist regions to create a waist opening and a pair of leg openings about the wearer. The shape of the fasteners may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener includes a separate piece of hook material affixed to the inside surface of a flexible backing.

The various regions and/or components of the diaper 100 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 104 and bodyside liner 102 are assembled to each other and to the absorbent core using an adhesive. Alternatively, the absorbent core may be connected to the outer cover 104 using conventional fasteners, such as buttons, hook and loop type fasteners, adhesive tape fasteners, and so forth. Similarly, other diaper components, such as the leg elastic members 106, waist elastic members 108 and fasteners, may also be assembled into the diaper 100 using any attachment mechanism.

III. Attachment Mechanisms

Figure 7:
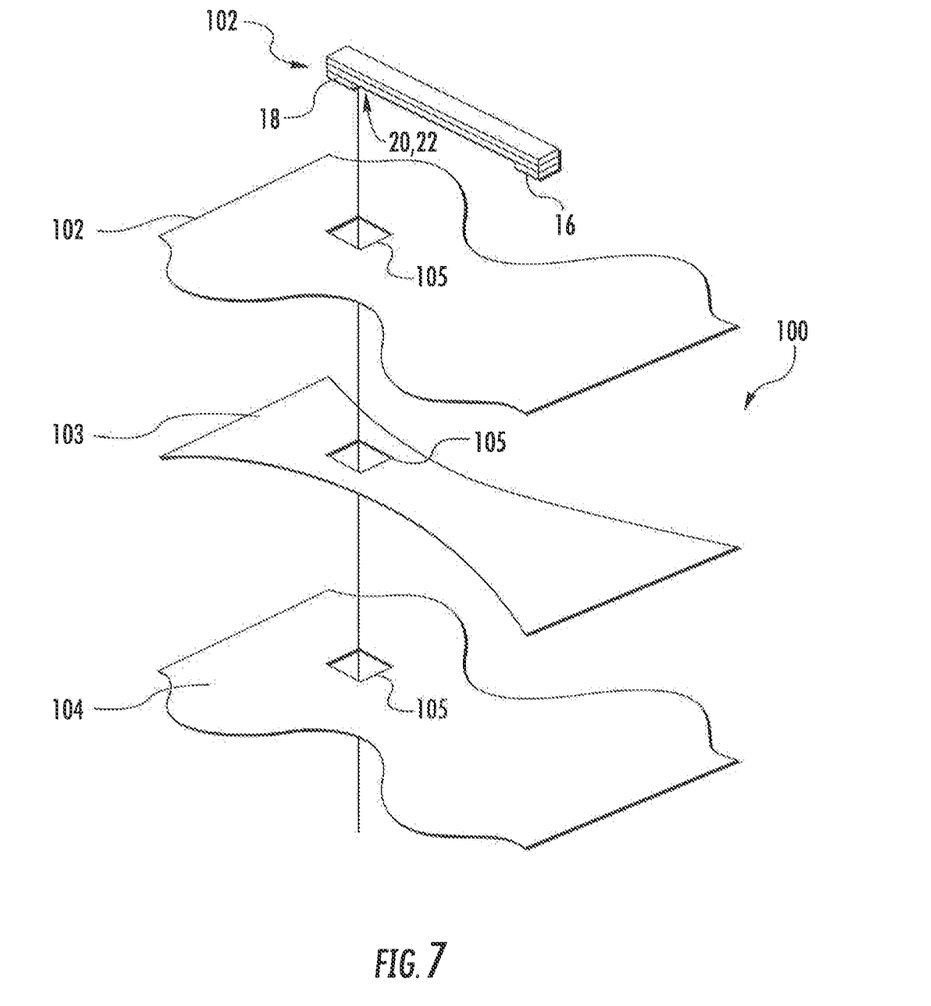
FIG. 7 is a perspective, exploded view of an absorbent article for attaching to a lateral flow device in accordance with one embodiment of the present invention.

Generally speaking, the lateral flow assay device may be attached onto the absorbent article in a variety of different orientations and configurations, so long as the device is capable of receiving the bodily fluid and providing a signal to a user or caregiver of the presence or absence of the analyte. In one embodiment, the detection zone and/or control zone can be visible to the user or caregiver so that a simple, accurate, and rapid indication of the presence of the analyte may be provided even when the absorbent article is being worn. The visibility of such zone(s) may be accomplished in a variety of ways. For example, in some embodiments, the absorbent article may include a transparent or translucent portion (e.g., window, film, etc.) that allows the detection zone and/or control zone to be readily viewed without removal of the absorbent article from the wearer. In this embodiment, each layer of the absorbent article can have a transparent material, such the detection zone and/or control zone of the lateral flow device can be visualized even when the device is positioned on the bodyside liner. For example, referring to FIG. 7, each layer of the exemplary diaper 100 has a transparent portion allowing viewing of the detection zone 20 and control zone 22 through its entire construction. As shown, the bodyside liner 102, the absorbent core 103, and the outer cover 104 have a transparent window 105 that are aligned to allow viewing through the diaper 100. In other embodiments, the detection zone and/or control zone may extend through a hole or aperture in the absorbent article for observation. In still other embodiments, the detection zone and/or control zone may be extended out of the absorbent article through the waist or leg region when worn by the user.

Alternatively, the lateral flow device can be attached to the absorbent article such that the signal is not visible until removal of the absorbent article from the wearer. For example, the device can be attached to the bodyside liner 102 such that the entire lateral flow device is concealed when the absorbent article is in use. Then, when the absorbent article is removed, the user or caregiver can read the signal displayed on the device.

For instance, referring to FIG. 4, a lateral flow assay device 10 may be attached to the bodyside liner 102. The sample zone 16, positioned at one end of the assay device 10, is strategically positioned in the diaper 100 so that urine discharged by the wearer can travel to the sample zone 16 for collection of at least a portion of the discharged urine therein. The absorbent material 18 is also provided at the other end of the assay device 10 to hold part of the sample and to promote wicking or capillary flow in the device 10.

In one particular embodiment, the device 10 is positioned on the bodyside liner 102 such that the application zone 16 is located towards the crotch region for contact with discharged urine, and the absorbent material 18 is positioned towards the waist region of the diaper 100. As such, the detection zone 20 and the control zone 22 are positioned away from the crotch region of the diaper, helping to inhibit any contamination from the urine discharged by the wearer.

FIG. 4 illustrates the assay device 10 as being placed directly onto the bodyside liner 102 of the absorbent article 100. Alternatively, the assay device 10 may be partially or completely encased within a thin film (not shown) except for the sample zone 16, which remains exposed to the bodily fluid (e.g., urine) being tested. Such embodiments may be desirable so as to inhibit other components of the assay device 10, other than the sample zone 16, from receiving the bodily fluid directly from the wearer or from the layers of the absorbent article 100. For example, the assay device 10 may operate more effectively if the wicking zone is shielded so that it draws the bodily fluid only from sample zone 16 and not from the absorbent article 100. Such thin film may be constructed, for example, from a variety of materials including polymers such as polyethylene, polypropylene, polycarbonate, and others.

For each of the embodiments described above, the assay device 10 may be attached onto the absorbent article using a variety of techniques or mechanisms. For example, the assay device 10 may be attached using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. Alternatively, the assay device 10 may be connected using conventional fasteners, such as buttons, hook and loop type fasteners, adhesive tape fasteners, and so forth. By way of further example, pockets or apertures may be built into one or more layers of the absorbent article to fix the position of the assay device 10. In short, a variety of configurations may be used to secure assay device 10 into a position that helps ensure contact with the bodily fluid to be tested.

Figure 2:
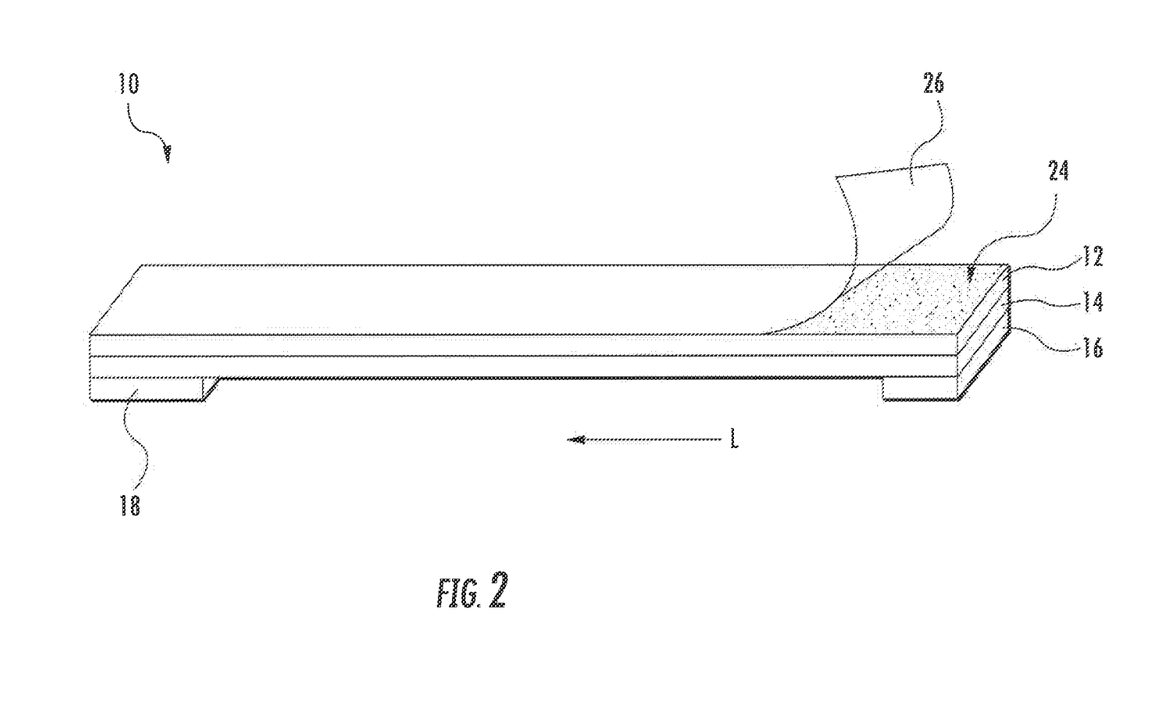
FIG. 2 is a perspective view of an exemplary attachment mechanism of the lateral flow device in accordance with one embodiment of the present invention.

For example, referring to the embodiment shown in FIG. 2, the lateral flow device 10 has an adhesive layer 24 applied to the backside of support 12. Adhesive layer 24 is shown protected with a peel strip 26 covering the adhesive layer 24, which can be peeled away to expose the adhesive layer 24 when the user is preparing to adhere device 10 to the absorbent article. The peel strip 26 can be any suitable layer, such as a film or fibrous web configured to release from the adhesive layer 24 while protecting its adherence capabilities.

Figure 3:
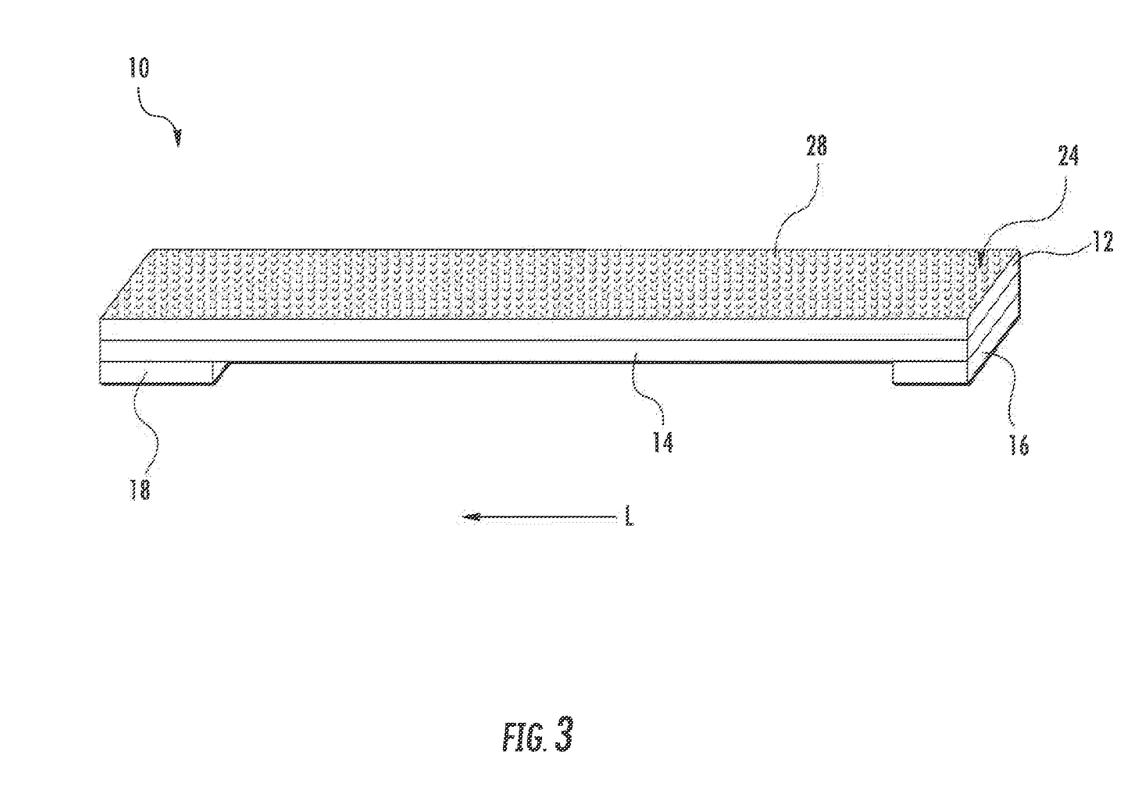
FIG. 3 is a perspective view of another exemplary attachment mechanism of the lateral flow device in accordance with one embodiment of the present invention.

In another embodiment, such as the exemplary embodiment shown in FIG. 3, the device 10 is shown having hook-like elements 28 for use in attaching to the bodyside liner of an absorbent article. The hook-like elements 28 can be those typically used in a hook and loop fastener, and may sufficiently attach to a bodyside liner formed from a nonwoven web, since the nonwoven web can have sufficient spaces between fibers for the hook-like elements 28 to attach. However, the absorbent article can be configured for attachment to the hook-like elements 28 by having loop-like elements located on the absorbent article (such as on the bodyside liner). Alternatively, the absorbent article can be configured with a loop-like structure located on the bodyside liner 102 to engage the hook-like elements 28 of the device 10.

In other embodiments, the absorbent article 100 can be configured to attach to a lateral flow device 10. For example, the absorbent article can be provided with an adhesive protected by a peel strip, such that the adhesive can be adhered to the later flow device when exposed.

In another embodiment, the later flow device can be provided within an insert. The lateral flow device can be incorporated within the insert in any manner, as long as a reading of the detection zone and control zone can be accomplished. For example, the lateral flow device can be placed just below the cover, and the area of the liner where the detection zone and the control zone are located can be transparent such that the signal can be read or viewed.

Figure 5:
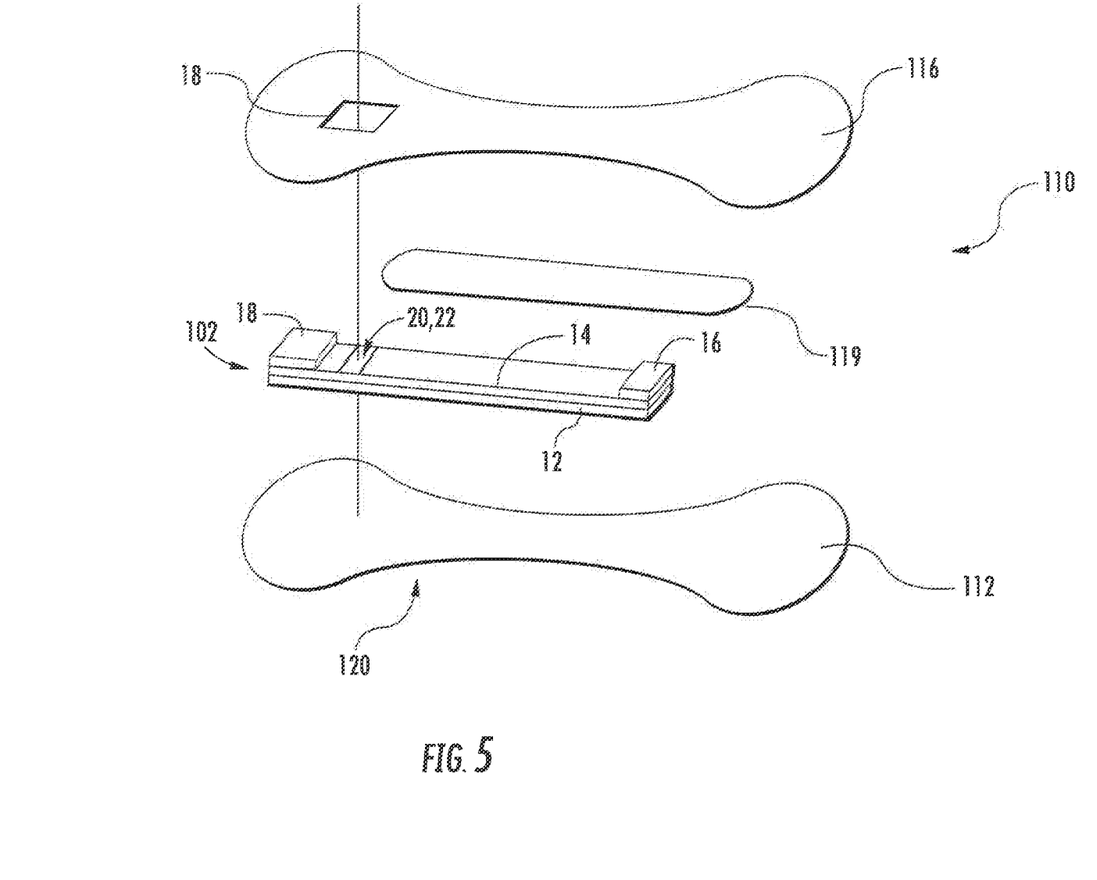
FIG. 5 is a perspective exploded view of an exemplary absorbent insert containing a lateral flow device for use with an absorbent article in accordance with one embodiment of the present invention.

For example, referring to the exemplary embodiment shown in FIG. 5, an insert 110 is provided with absorbent material 114 positioned encased within a cover formed from a back coversheet 112 and a top coversheet 116. The lateral flow device 10 is shown positioned between the back coversheet 112 and the absorbent material 114. The back coversheet 112 is provided on its exposed side 110 with an adhesive layer configured to adhere the insert 110 to the bodyside liner of an absorbent article. As such, the insert 110 can be positioned between the bodyside liner of an absorbent article and the skin of the wearer. Thus, upon insult of the absorbent article by the wearer, the insert 110 is wetted with urine, and the application zone 16 of the lateral flow device 10 can contact a sufficient amount of urine.

In one particular embodiment, the absorbent capacity of the absorbent insert 110 can be less than that of the absorbent article to which it is attached. As such, the absorbent core of the absorbent article can attract a majority of insulting fluid. However, the absorbency of the absorbent insert 110 is sufficient to provide enough of the insulting fluid to the lateral flow device 10 for a sufficient reading. In one embodiment, for instance, the absorbent insert can be substantially free from superabsorbent material. Accordingly, the absorbent insert can be configured to absorb less than 20% of total bodily fluid absorbed by the absorbent article and the absorbent insert, such as less than about 15%. In some embodiments, the absorbent insert is configured to absorb less than 10% of total bodily fluid absorbed by the absorbent article and the absorbent insert, such as less than about 5%.

Although the insert is disclosed as including absorbent material 114, it is to be understood that the insert does not have to include any absorbent material. For example, in one embodiment, the insert can simply be constructed of the lateral flow device encased within a cover. In either embodiment, the top coversheet 116 can be similarly constructed to that of any bodyside liner of an absorbent article, such as those bodyside liners described above with reference to the absorbent articles. Likewise, the back coversheet 112 can be similar to those outer covers described above with reference to the absorbent article. However, in some embodiments, the back coversheet 112 can be liquid permeable, allowing the bodily fluid to defuse through the back coversheet 112, and into the absorbent article to which it is attached. Thus, in some embodiments, the back coversheet 112 can be constructed of any material described above with reference to the bodyside liners of the absorbent articles. In one particular embodiment, the back coversheet 112 and the top coversheet 116 are constructed of the same material.

Figure 6:
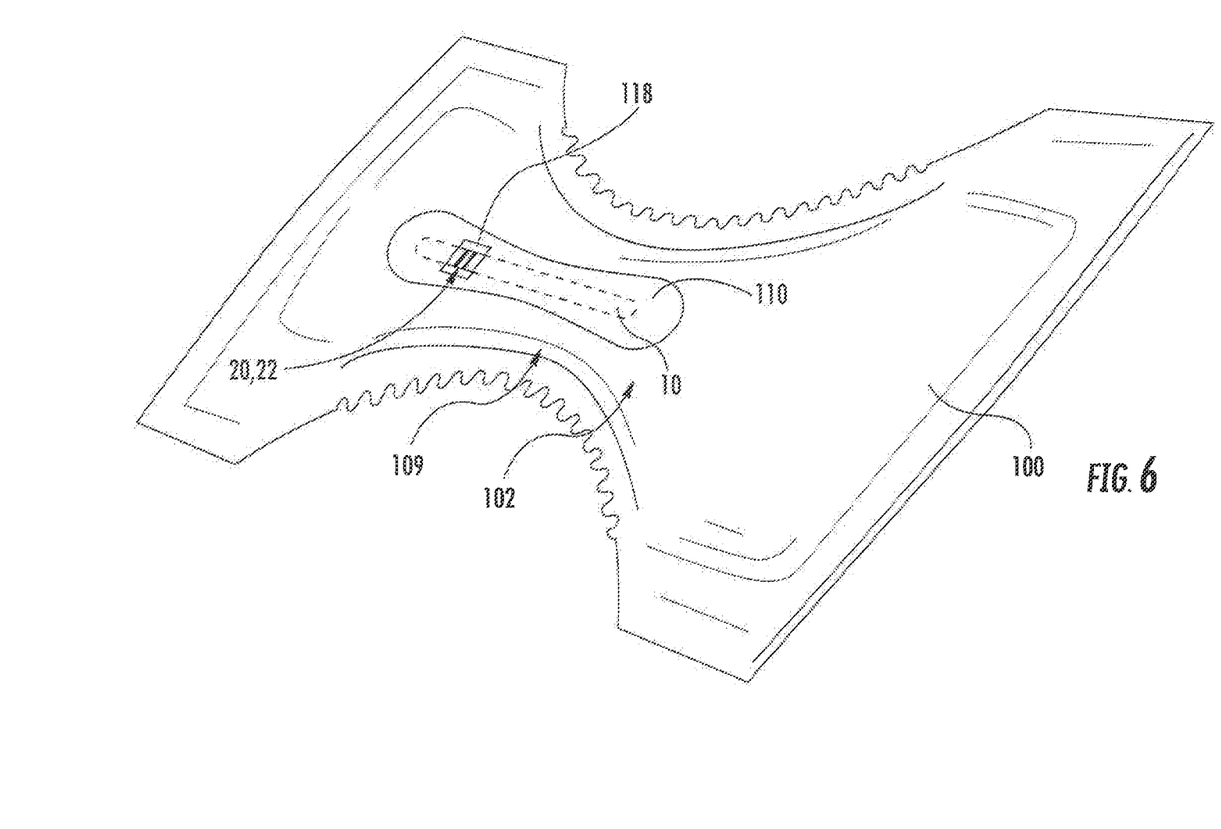
FIG. 6 is a perspective view of an absorbent insert containing a lateral flow device attached to an absorbent article in accordance with one embodiment of the present invention.

In one particular embodiment, the top coversheet 116 can be provided with a transparent window 118 enabling the user or caregiver to view the detection zone 20 and the control zone 22 through the bodyside liner 116. Thus, upon removal of the absorbent article having the absorbent insert attached thereto, the user can visually inspect the lateral flow device 10 to determine the presence or absence of the targeted analyte. Referring now to the exemplary embodiment shown in FIG. 6, the absorbent 110 is adhered to absorbent article 100. The insert 110 is shown having a transparent window 118 for viewing the detection zone 20 and the control zone 22 of the lateral flow device 10 located within the construction of the insert 110. Various methods can be utilized to attach the insert 110 to the absorbent article 100. For example, the absorbent insert 110 can be adhered to the bodyside liner 102 of the absorbent article 100. Alternatively, the absorbent insert 110 can be mechanically fastened to the absorbent article, such as through the use of hook and loop fasteners and the like.

IV. Kits and Methods

In one embodiment, the lateral flow device can be provided in a kit including both the device and an absorbent article. As discussed above, the lateral flow device can be provided with or without an attachment mechanism attached to it, or may be provided within the construction of an absorbent insert. Likewise, the absorbent article may be provided with an attachment mechanism configured to be attached to the lateral flow device or absorbent insert. Thus, the kit can include any number of configurations of a lateral flow device and an absorbent insert, as long as the combination allows for attachment of the lateral flow device to the absorbent article.

In yet another embodiment, a method for detecting the presence or absence of an analyte in a bodily fluid, such as urine, is generally disclosed. The method can include attaching a lateral flow device to a bodyside liner of an absorbent article. Any of the lateral flow devices described above can be attached to any of the absorbent articles described above. As such, any of a variety of different combinations of lateral flow devices and absorbent articles can be used within the method.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article for testing a bodily fluid suspected of containing an analyte, the absorbent article comprising:
   an outer cover;
   a bodyside liner;
   an absorbent core positioned between the outer cover and the bodyside liner; and
   an insert for testing the bodily fluid suspected of containing the analyte, the insert comprising a cover, a lateral flow device encased within the cover, and an attachment mechanism for attaching a liquid permeable back coversheet of the insert to the bodyside liner of the absorbent article, wherein the lateral flow device comprises a chromatographic medium that defines a detection zone, the detection zone being configured for exhibiting a signal indicative of the presence or absence of the analyte in the bodily fluid, wherein the lateral flow device is configured to perform a heterogeneous assay in which one species is separated from another species prior to detection, the lateral flow device further including a first absorbent area and a second absorbent area, the second absorbent area being positioned downstream to receive a bodily fluid after flowing through the chromatographic medium.

2. An absorbent article as in claim 1, wherein the liquid permeable back coversheet of the insert is releasably attached to the bodyside liner of the absorbent article.

3. An absorbent article as in claim 1, wherein the chromatographic medium includes a control zone for indicating that a sufficient volume of the bodily fluid has been received by the lateral flow device.

4. An absorbent article as in claim 3, wherein the lateral flow device further comprises a control reagent that is capable of being detected within the control zone.

5. An absorbent article as in claim 1, wherein the lateral flow device further comprises a sample application zone.

6. An absorbent article as in claim 1, wherein the lateral flow device further comprises a capture reagent that is substantially non-diffusively immobilized within the detection zone.

7. An absorbent article as in claim 6, wherein the capture reagent is a specific binding member.

8. An absorbent article as in claim 6, wherein the capture reagent is a diazonium ion or a derivative thereof.

9. An absorbent article as in claim 6, wherein the lateral flow device further comprises a diffusively immobilized reagent.

10. An absorbent article as in claim 9, wherein the diffusively immobilized reagent includes a specific binding member.

11. An absorbent article as in claim 9, wherein the diffusively immobilized reagent includes an aromatic ester substrate.

12. An absorbent article as in claim 1, wherein the liquid permeable back coversheet of the insert is adhesively attached to the bodyside liner of the absorbent article.

13. An absorbent article as in claim 1, wherein the liquid permeable back coversheet of the insert is attached to the absorbent article using a hook and loop type fastener.

14. An absorbent article as in claim 1, wherein the liquid permeable back coversheet of the insert comprises hook-like members for attaching to the bodyside liner of the absorbent article.

15. An absorbent article as in claim 1, wherein the liquid permeable back coversheet of the insert comprises an adhesive layer on an exposed surface for attaching to the bodyside liner.

16. An absorbent article as in claim 1, wherein the insert further comprises absorbent material configured to absorb less than 20% of the bodily fluid discharged into the absorbent article.

17. An absorbent article as in claim 16, wherein the insert is substantially superabsorbent free.

18. An absorbent article as in claim 1, wherein the insert comprises a transparent window allowing the detection zone to be viewed by a user.

19. An absorbent article as in claim 1, wherein detection zone of the lateral flow device is capable of being viewed when the absorbent article is worn by a wearer.

20. An absorbent article as in claim 19, wherein each of the outer cover, the absorbent core, and the bodyside liner comprises a transparent window, and wherein the outer cover, the absorbent core, the bodyside liner, and the lateral flow device are arranged such that the detection zone of the lateral flow device is viewable through the transparent window when the absorbent article is worn by a wearer.

21. The absorbent article of claim 1, wherein the analyte comprises a leukocyte esterase.

22. An insert for testing a bodily fluid suspected of containing an analyte, the insert comprising:
a cover;
a lateral flow device encased within the cover, the lateral flow device comprising a chromatographic medium that defines a detection zone, the detection zone being configured for exhibiting a signal indicative of the presence or absence of the analyte in the bodily fluid, wherein the lateral flow device is configured to perform a heterogeneous assay in which one species is separated from another species prior to detection, the lateral flow device further including a first absorbent area and a second absorbent area, the second absorbent area being positioned downstream to receive a bodily fluid after flowing through the chromatographic medium; and
an attachment mechanism configured to attach a liquid permeable back coversheet of the insert to a bodyside liner of an absorbent article.

23. The insert of claim 22, wherein the analyte comprises a leukocyte esterase.

24. A method for detecting the presence or absence of an analyte in urine, the method comprising:
attaching a liquid permeable back coversheet of an insert to a bodyside liner of an absorbent article, the insert comprising a cover and a lateral flow device encased within the cover, wherein the lateral flow device comprises a chromatographic medium that defines a detection zone, the detection zone being configured for exhibiting a signal indicative of the presence or absence of the analyte in the bodily fluid, wherein the liquid permeable back coversheet of the insert or the absorbent article comprises an attachment mechanism, wherein the lateral flow device is configured to perform a heterogeneous assay in which one species is separated from another species prior to detection, the lateral flow device further including a first absorbent area and a second absorbent area, the second absorbent area being positioned downstream to receive a bodily fluid after flowing through the chromatographic medium.

25. The method of claim 24, wherein the analyte comprises a leukocyte esterase.

* * * * *